US009881110B1

(12) United States Patent
Mohajerin (10) Patent No.: US 9,881,110 B1
(45) Date of Patent: Jan. 30, 2018

(54) APPARATUS AND METHOD FOR ESTIMATING AND MODELING TURBULENT FLOW

(71) Applicant: Sohrab Mohajerin, Pleasanton, CA (US)

(72) Inventor: Sohrab Mohajerin, Pleasanton, CA (US)

( * ) Notice: Subject to any disclaimer, the term of this patent is extended or adjusted under 35 U.S.C. 154(b) by 121 days.

(21) Appl. No.: 14/927,215

(22) Filed: Oct. 29, 2015

(51) Int. Cl.
*G06F 17/50* (2006.01)
*G06F 17/18* (2006.01)

(52) U.S. Cl.
CPC .......... *G06F 17/5009* (2013.01); *G06F 17/18* (2013.01); *G06T 2210/24* (2013.01)

(58) Field of Classification Search
CPC . G06F 17/5009; G06F 2217/16; G06T 13/60; G06T 2210/24
USPC ............................................................ 703/9
See application file for complete search history.

(56) References Cited

U.S. PATENT DOCUMENTS

| | | | | | |
|---|---|---|---|---|---|
| 5,801,969 | A * | 9/1998 | Nagahama | ............... | G06F 17/13 703/9 |
| 6,516,292 | B2 * | 2/2003 | Yahalom | .................. | G06F 17/10 345/419 |
| 7,120,544 | B2 * | 10/2006 | Duncan | ................ | G06F 17/5018 702/50 |
| 7,130,782 | B2 * | 10/2006 | Miyori | ................ | G06F 17/5018 473/199 |
| 7,150,202 | B2 * | 12/2006 | Gysling | .................... | G01F 1/74 702/45 |
| 7,243,057 | B2 * | 7/2007 | Houston | ............. | G06F 17/5018 703/2 |
| 7,472,046 | B2 * | 12/2008 | Rasmussen | ......... | G06F 17/5018 345/473 |
| 7,565,276 | B2 * | 7/2009 | Song | .................... | G06F 17/5018 345/474 |
| 7,668,705 | B2 * | 2/2010 | Kalitzin | .............. | G06F 17/5018 703/2 |
| 7,724,258 | B2 * | 5/2010 | Ebert | ...................... | G06T 13/60 345/419 |
| 7,930,945 | B2 * | 4/2011 | Stange | ...................... | G01F 1/60 73/861.11 |
| 8,099,265 | B2 * | 1/2012 | Houston | ................. | G01P 5/001 345/420 |
| 8,775,140 | B2 * | 7/2014 | Yu | ........................... | G06F 17/13 703/2 |
| 9,031,819 | B2 * | 5/2015 | Chen | ................... | G06F 17/5018 703/9 |
| 9,111,056 | B2 * | 8/2015 | Hong | .................. | G06F 17/5009 |

(Continued)

FOREIGN PATENT DOCUMENTS

DE     19902573 A1 *  7/2000  ............ G01M 10/00

*Primary Examiner* — John Villecco
(74) *Attorney, Agent, or Firm* — File-EE-Patents.com; Jay A. Chesavage (57) ABSTRACT

A turbulent flow estimation apparatus and method provides for the measurement of turbulent flow through the introduction of particles which characterize the flow, the detection of extents of turbulent flow regions, the assignment of a plurality of primitive shapes to those turbulent flow regions, and the assignment of individual characteristics to each of the primitive shapes of the estimate, including center location, rotational velocity of the primitive shape, identification of the rotational axis of the primitive shape, and the temporal trajectory of the primitive shapes.

22 Claims, 8 Drawing Sheets

(56) References Cited

U.S. PATENT DOCUMENTS

| | | | |
|---|---|---|---|
| 9,135,379 B2* | 9/2015 | Williams | G06F 17/5009 |
| 9,223,909 B2* | 12/2015 | Chen | G06F 17/5018 |
| 9,542,506 B2* | 1/2017 | Chen | G06F 17/5009 |
| 9,727,999 B2* | 8/2017 | Olivan Bescos | G06T 15/00 |
| 2007/0219766 A1* | 9/2007 | Duggleby | G06F 9/3879 |
| | | | 703/9 |
| 2008/0126045 A1* | 5/2008 | Shan | G06F 17/5018 |
| | | | 703/9 |
| 2009/0234595 A1* | 9/2009 | Okcay | G01M 9/067 |
| | | | 702/49 |
| 2010/0045669 A1* | 2/2010 | Johnson | G06T 13/60 |
| | | | 345/420 |
| 2010/0185420 A1* | 7/2010 | Ding | G06F 17/5018 |
| | | | 703/2 |
| 2011/0009745 A1* | 1/2011 | Seifer | G01F 1/74 |
| | | | 600/437 |
| 2012/0245910 A1* | 9/2012 | Rajnarayan | G06F 17/5018 |
| | | | 703/9 |
| 2012/0313938 A1 | 12/2012 | Mohajerin | |
| 2017/0132048 A1* | 5/2017 | Suwa | G06F 9/5066 |
| 2017/0177759 A1* | 6/2017 | Kim | G06F 17/5018 |

* cited by examiner

*Figure 1A*

*Figure 1B*
Y-Z Plane

*Figure 1C*
X-Z Plane

*Figure 1D*

*Figure 2A*
Y-Z Plane

*Figure 2B*
X-Z Plane

*Figure 5A*
Model Estimation Process: Pre decimation

*Figure 5B*
Model Estimation Process

*Figure 5C*
Model Estimation Process

Figure 5D
Turbulence Model

Figure 5E

Figure 5F
Model Estimation Process

Figure 6A
Toroidal Flow Example

Figure 6B
Toroidal Flow Example

Figure 7A
Toroidal Flow Example

Figure 7B
Toroidal Flow Example

APPARATUS AND METHOD FOR ESTIMATING AND MODELING TURBULENT FLOW

FIELD OF THE INVENTION

The present invention relates to the estimation and modeling of turbulent flow. In particular, the invention relates to measurement of flow in a three dimensional volume and the generation of a mathematical and topographical model to estimate the turbulent flow in the three dimensional volume.

BACKGROUND OF THE INVENTION

Turbulent flow is problematic to model because of its typically random and time-variant behavior, as well as the non-linear trajectories of flow and turbulent components of flow. A prior art method of describing flow is to divide the flow components into laminar flow regions and turbulent flow regions, where the turbulent flow is characterized by Reynolds number, the ratio of momentum forces to viscous forces. It is desired to provide a model for turbulent flow, and additionally desired to provide a memory-efficient description for the estimation of turbulent flow.

OBJECTS OF THE INVENTION

A first object of the invention is a method for the estimation and modeling of turbulent flow in a three dimensional volume using a plurality of discrete primitive shapes.

A second object of the invention is a method for the estimation and modeling of turbulent flow in a three dimensional volume using a plurality of continuous primitive shapes.

SUMMARY OF THE INVENTION

A three dimensional (3D) flow to be modeled is infused with particles, and the particle motion is examined using cameras or other sensors to discern particle position and velocity, and eddy flow extents in particular regions of interest in a volume of fluid flow. The volume may be formed into planar two dimensional (2D) slabs which may then be combined individually to form the 3D model, or the volume may be modeled as a 3D volume directly. In a 3D example of the invention, flow eddies and circulations are characterized and modeled as primitive shapes which are either discrete in the form of polyhedrons which are determined by the position of particles in an eddy flow extent, or as continuous and in the form of spherical, toroidal, or ellipsoidal shapes or other suitable shapes that indicate the movement particles based on actual trajectories of the particles within an eddy flow extent.

From a complete dataset of particles and particle movement which are acquired during a data acquisition interval, datasets are extracted and organized into primitive shapes, including 2D or 3D multi-faceted discrete shapes defined by vertices at each face of the shape, the vertices formed by the largest extent of the multi-faceted forms which rotate, tumble, or otherwise evolve in trajectory through the fluid flow. Alternatively, the primitive shapes may be defined as continuous shapes such as circular or elliptical shapes which model the particle flow trajectories. By providing these primitive shapes in the form of multi-faceted polyhedral shapes or continuous surface shapes, and defining a linear translational movement as well as a rotational movement, a plurality of such primitive shapes may be formed into a model which describes the turbulent flow using a comparatively small number of primitive shape objects. Each primitive shape may be described by vertices defined by the particles after a reduction operation which identifies appropriate primitive shapes based on an error metric which may be chosen based on minimal error between the model and the particle movement, or which may allow a larger error between the model and particle movement so as to simplify the number and complexity of the primitive shapes. The process of classification into primitive shapes may rely on previous classification results based on identified eddy flows, or the classification may be started afresh with each pair of image acquisitions which identifies particle positions and velocities.

DETAILED DESCRIPTION OF THE INVENTION

Figure 1A:
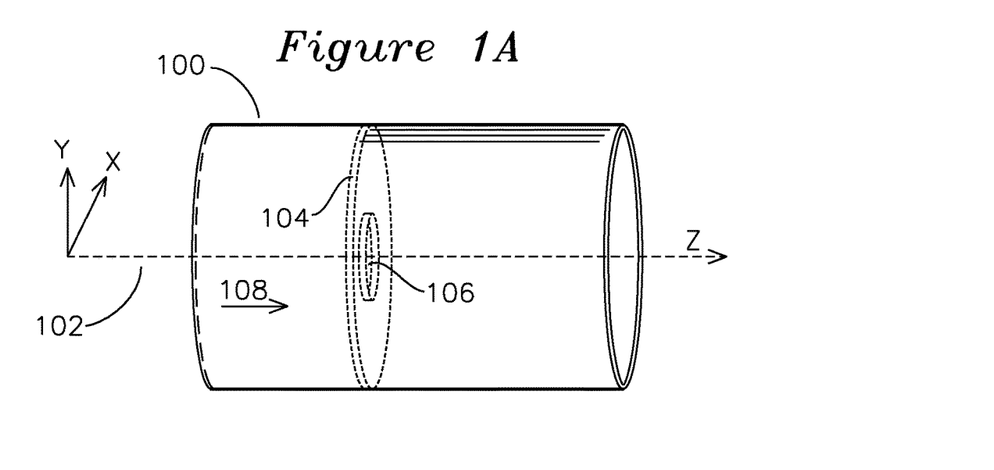
FIG. 1A is a section view of a 3D volume having an X, Y, and Z axis, showing a 2D section through a tube carrying a fluid through a barrier which creates a turbulent flow.

FIG. 1A shows a cylinder 100 having an aperture 106 and a fluid 108 moving initially in the direction of the Z axis as shown. The fluid being conveyed may be any fluid subject to the laws of fluid dynamics, including a gas or a liquid, such as having the property of generating eddies or eddy flows over an eddy flow extent and other non-laminar flow patterns after a flow disruption such as is created by aperture 106.

Figure 1B:
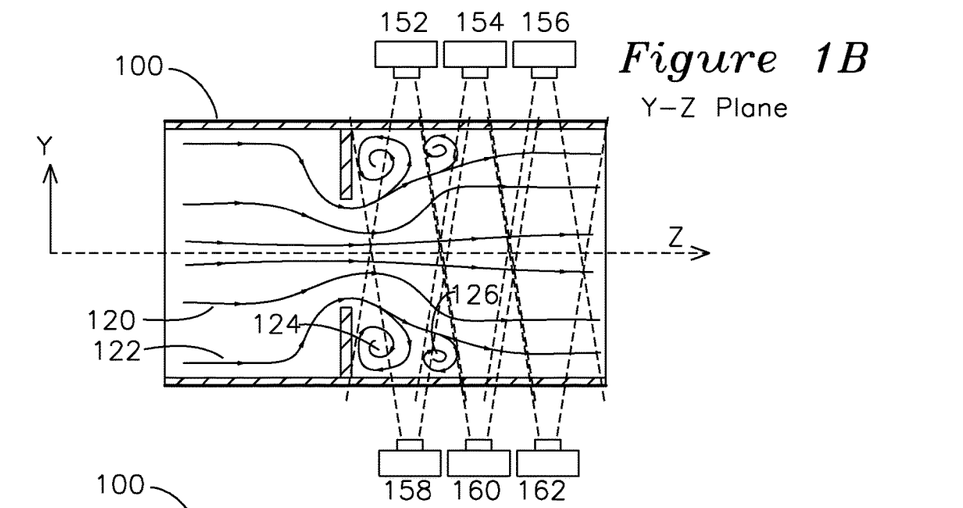
FIG. 1B is a section view of FIG. 1A through the Y-Z plane showing turbulent flow.
Figure 1C:
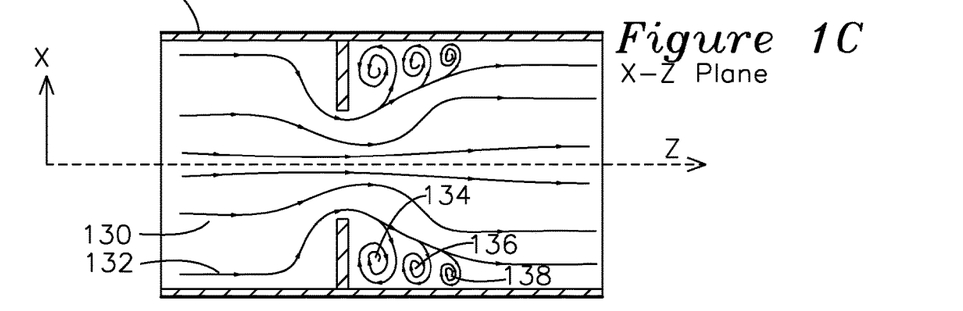
FIG. 1C shows a section view of FIG. 1A through the X-Z plane showing turbulent flow.
Figure 1D:
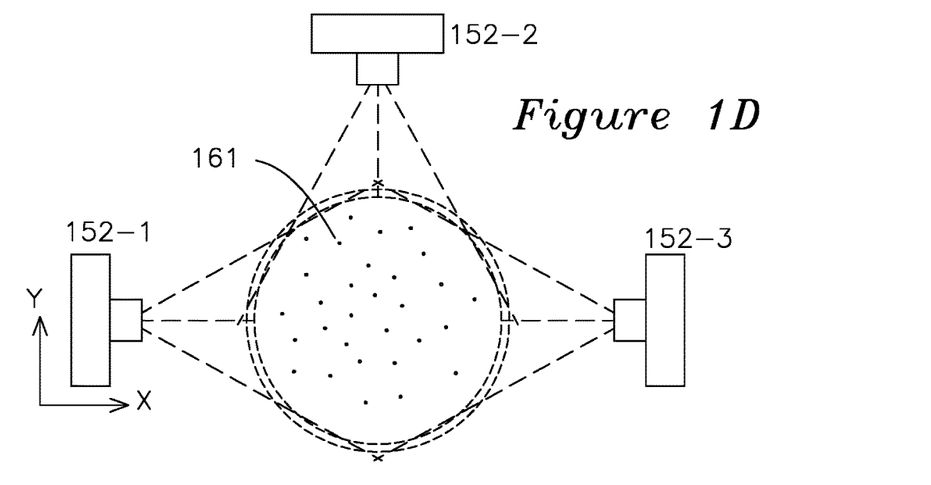
FIG. 1D shows an optical detector system for acquiring orthogonal views of particle images.

The image acquisition and resolution of individual particles into 3D particle locations in real-time may be performed where the flow channel 100 is transparent and the particle images captured by cameras 152, 154, 156, 158, and 162 as shown in FIG. 1B, and the axial arrangement may be as shown in FIG. 1D where a particular camera 152 of FIG. 1B is represented by an axial surround of cameras 152-1, 152-2, and 152-3. Other arrangements and locations along the z axis and y-z axis are possible, the examples of FIGS. 1B and 1D are shown to illustrate an example optical detector system for locating in 3D space each of the trace particles to be imaged, such as particle 161 of FIG. 1D. The camera images and associated optics may include compensation for the refractive index change into the fluid where the fluid has a different refractive index than air, for the example of a camera imaging a liquid, and the cameras optics may be integrated into the flow chamber in a manner which does not introduce turbulence apart from the turbulence to be measured. The camera optics may further incorporate refractive index matching to avoid parallax-related position estimation errors associated with the channel 100 or the fluid contained by channel 100. The image detectors 152, 154, 156, 158, 160, and 162 may acquire a succession of images in time which provide information about the location and instantaneous velocity of each particle for use in the steps of the model.

The flow pattern generated is a three dimensional flow, but for clarity in understanding the invention, FIG. 1B shows a 2D cross section visualization of flow through the cylinder 100 and aperture 106 of FIG. 1A in the y-z plane. Eddy flow and circular flow patterns 124 and 126 may occur in flow path 122, whereas other flow paths such as 120 may be relatively unperturbed and follow laminar flow behaviors. In three dimensions, these flows may be modeled as a series of continuous primitive shapes such as ellipsoids, toroids, or other three dimensional solids which have a rotational axis and a direction of translation which may model the swirling circular currents as they evolve through the z axis. For example, eddy flow 126 may have started as a circular eddy flow 124 at an earlier point in time, with both eddy flow 124 and eddy flow 126 propagating down the Z axis, changing shape and enclosed volume during this evolution, with new circular eddys being launched by the turbulence behind aperture 106, with the eddy flows damping out and returning to laminar flow further down the z axis direction.

Alternatively, the flows may be modeled as a plurality of discrete primitive shape polyhedrons in the (x, y, z) volume, each faceted surface primitive shape and each continuous surface primitive shape having a series of associated parameters, including velocity, rotation rate, scale factor, time-dependent evolution factor, or other parameters which affect shape, rotation, and translation through space over time.

In accordance with the objects of the invention, the flow patterns of the turbulent flow shown in 124 and 126 of FIG. 1B and the flows of 134, 136, and 138 may be represented by primitive faceted or continuous shapes, each having associated rotational and translational parameters. A first step in visualizing the eddy flows is the characterization of eddy flow patterns by observation with the assistance of visual matter added to the fluid. This may be done by introducing tracing particles into the flow, subject to the requirement that the tracing particles may be tracked individually within the eddy flows. Examples of suitable tracing particles for gasses include smoke or reflective particles of individually visible size such as small Styrofoam® balls which may be tracked through their trajectory through a series of instantaneous measurements as well as a progression of time-series images. Examples of suitable tracing particles for fluids include colored dye injected into the flow for macroscopic measurements, or metal flakes such as titanium or other lightweight particles for microscopic measurements. It is understood that for gasses or liquids, the key property is that the introduced particles have substantially the same density as the gas or liquid being studied, such that the particles are neither comparatively buoyant nor denser than the surrounding fluid, which would affect the flow measurement and resulting estimate.

FIG. 1C shows a planar section of a flow profile in the perpendicular X-Z plane, which has a three evolving eddy flows 134, 136, and 138, compared to the two evolving eddy flows 124 and 126 of FIG. 1B.

Figure 2A:
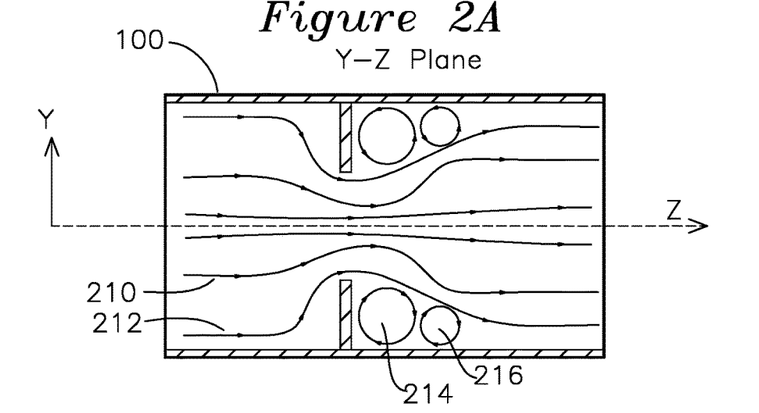
FIG. 2A shows a section view of FIG. 1B showing estimated flows.
Figure 2B:
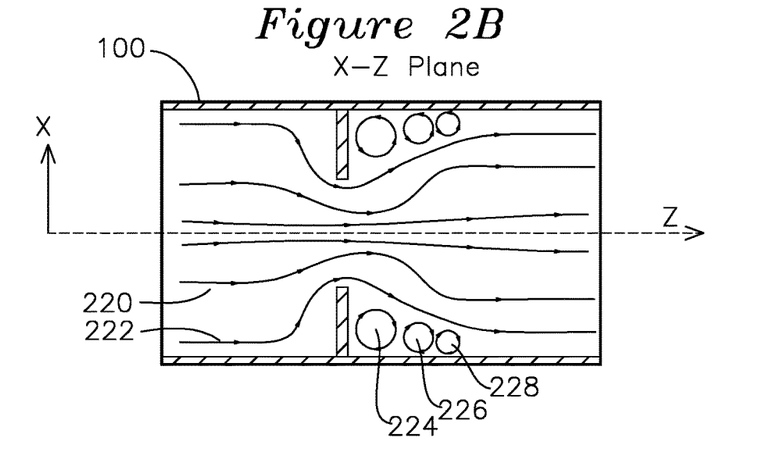
FIG. 2B shows a section view of FIG. 1C showing estimated flows.

FIG. 2A shows a planar section of a 3D volume with an estimate of turbulent flow of FIG. 1B, showing primitive shapes 214 and 216 used to model the turbulent flow and curvi-linear flow paths 210 and 212. FIG. 2B shows the corresponding estimate of flows of measured flows of FIG. 1C, with primitive shapes 224, 226, and 228 representing the flow estimate and extent as well as curvi-linear flow paths 220 and 222.

The types and classes of primitive shapes may be quite extensive, and depend on the particular volume being estimated. For example, while circular primitive shapes are shown for the 2D case in 214, 216, 224, 226, and 228 of FIGS. 2A and 2B, many other types of primitive shapes may be alternatively used including polyhedrons formed from adjacent polygons, or any suitable polyhedron formed in three dimensional space with a plurality of coincident vertices. For use in studying the 3D flow case, the primitive shapes may include not only discrete surface primitive shapes such as polyhedrons with any number of vertices, but also continuous surface primitive shapes such as spheres, ellipsoids, or other continuous surface shapes which may be used to model the flow. Additionally, mixtures of different types of primitive shapes may be used.

The flow estimation model may include a plurality of primitive shapes, each primitive shape having one or more associated parameters, including:

a) center point of the primitive shape, indicating a reference point in the primitive shape with respect to x,y, and z axes;

b) a rotational rate φ for the primitive shape, the rotational rate having an axis of rotation about the center, the axis of rotation being with respect to the x,y, and z axes;

c) translation rate v of the primitive shape with respect to the center, the translation rate being a velocity with respect to the x, y and z axes;

d) a time-dependent scaling in x, y, and z of the primitive shape with respect to the center of the primitive shape;

e) for asymmetrical primitive shapes, a description of the shape and evolution of the shape over time. One example is an ellipsoid primitive shape where the particles elliptically rotate about the long axis of the ellipse, which maintains a long axis which is relatively fixed through the movement of particles, similar to a tank tread over an elliptical guide.

Figure 3A:
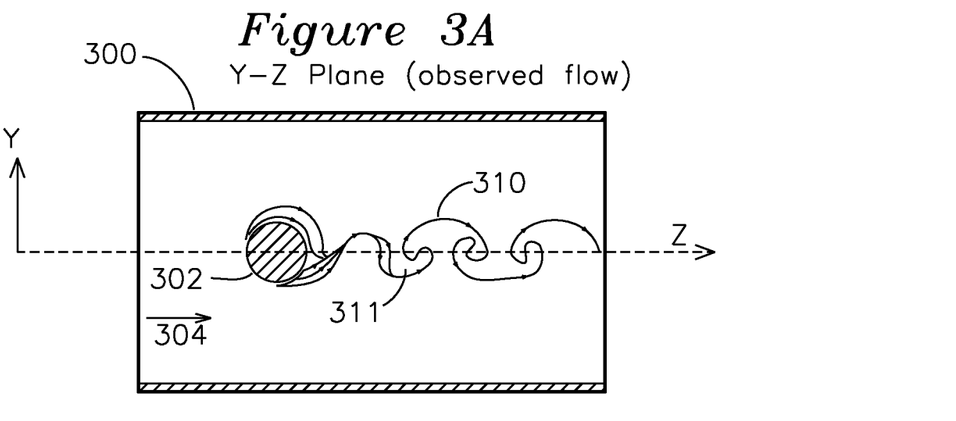
FIG. 3A shows a Y-Z plane section of turbulent flow created by a rod in a cylinder.

FIG. 3A shows a 2D cross section in the y-z plane of another 3D example flow, where flow 304 through a pipe 300 encounters a circular bar 302 which creates the flow shown in curve 310, including evolving folds 311, which tend to propagate down the z axis with the flow, and which may tend to reduce in y extent as they progress, with new folds forming behind the bar 302 as the nascent folds propagate down the z axis. The flow may be visualized using a dye or visible particles as was previously described. The surrounding flow continues along Z, however the evolving canonical re-entrant flow shapes of 311 continue along the Z axis as shown.

Figure 3B:
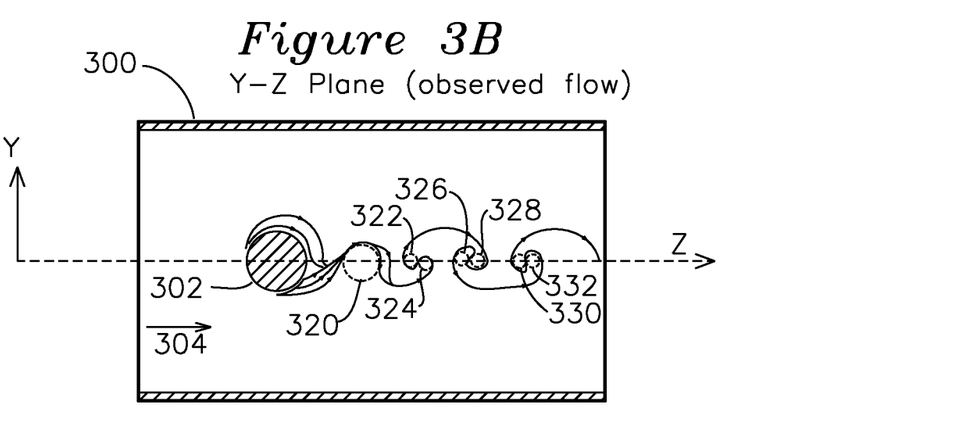
FIG. 3B shows a method of estimating flow trajectory for FIG. 3A.
Figure 3C:
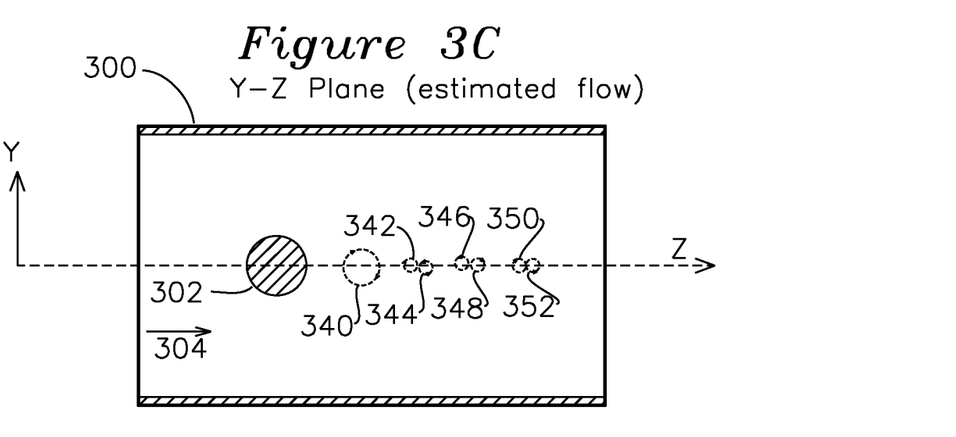
FIG. 3C shows estimated flow trajectory for FIG. 3B.

FIG. 3B shows an 2D view of an overlay of example primitive shapes 320, 322, 326, 328, 330, and 332, each of which has a Y,Z center coordinate, a rotational velocity φ, and optionally, a Y,Z position which evolves over time as the primitive shape proceeds with the flow along the Z axis. FIG. 3C shows a 2D section view of evolving 3D flow along the Z axis, with the turbulent flow modeled as primitive shapes 340, 342, 344, 346, 348, 350, and 352.

Figure 4:
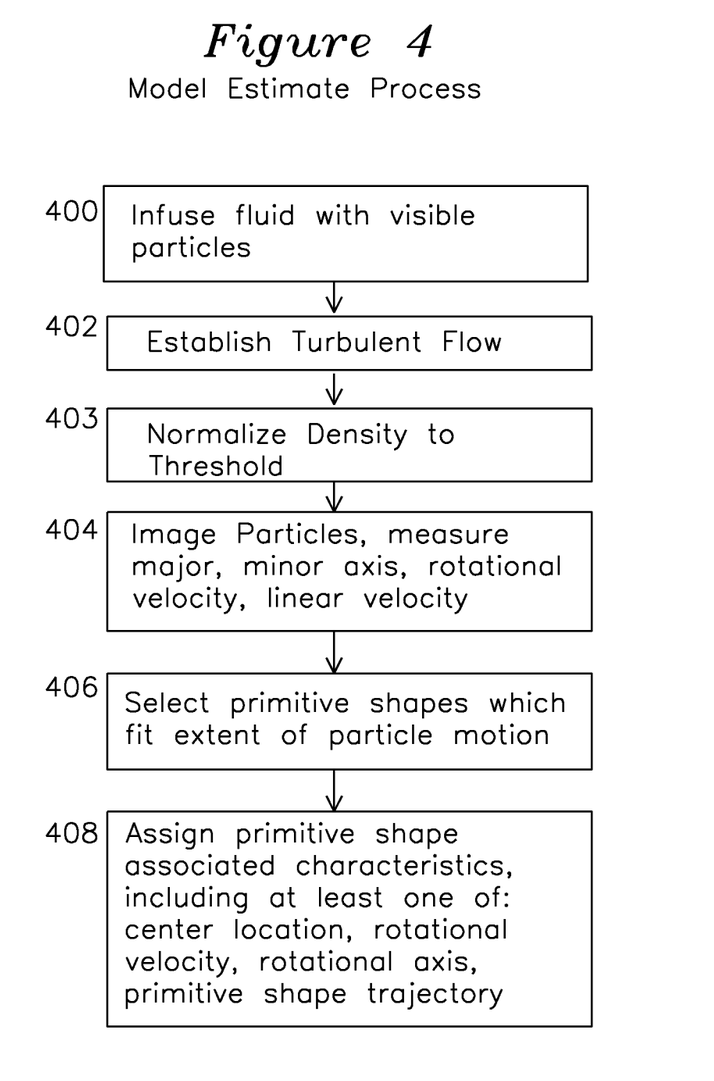
FIG. 4 is a flowchart for a flow estimation process.

FIG. 4 shows an estimation process for generating a model from observed flow. The fluid to be studied is infused with particles in step 400, and the turbulent flow is established in step 402 with the visible particle positions imaged at a rate sufficient to distinguish each particle as having a position and velocity vector P(x,y,z) 3D space, as was previously described. One or more images are concurrently acquired in step 404, and the particle positions and trajectories are detected and resolved, such as by using pairs of images and the tracking of particle movement between each image, with the time separation and (x,y,z) coordinate change indicating vector velocity.

Subsequently, a density equalization step 403 is performed, whereby the number of particles in a volume is compared to a settable threshold, and, in regions where the particle density exceeds the threshold, imaged particles are removed from further consideration until a threshold density is achieved.

Subsequently, using the imaged particles remaining after the density equalization step, eddy flow extents are identified, either for the purpose of selecting particles for use in a forming discrete primitive shapes, or for use in forming continuous primitive shapes. The eddy flow extent identification is performed with particular identification of the outer boundary of flow with the identification of an associated primitive shape in steps 404 and 406, where the candidate primitive shapes are compared against the flow characteristics, for example with regard to aspect ratio of the shape. In step 408, the primitive shape is associated with various characteristics, including at least one of center location, rotational velocity, a rotational axis, and a shape trajectory indicating the progression of the primitive shape over time.

Figure 5A:
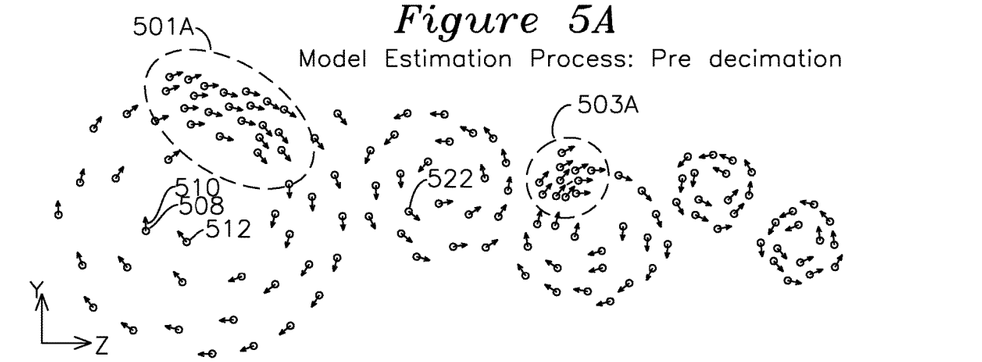
FIG. 5A shows an example distribution of particles, each with an associated velocity.

FIG. 5A shows the steps of FIG. 4 applied to an example initial simplified 2D example of observed particles in a 3D volume. A series of images of the particles or dye of FIG. 4 step 400 may be acquired with inter-image intervals short enough to discern individual and eddy flow extent group particle movements between image acquisitions at start of flow step 402. An example of such acquisition of step 404 of FIG. 4 is shown in FIG. 5E, which may rely on the images acquired using the example camera arrangement of FIGS. 1B and 1D, where each successive image acquisition 540, 542, 544, 546, and 548 resolves each particle location in x,y,z space, and these sequential image acquisitions are taken at sequential times t1, t2, t3, t4, and t5, respectively, and are thereafter analyzed in pairs to determine a velocity vector for each particle, shown generally as Vp(x,y,z) for respective velocity vector maps Vp 550, 552, 554, 556, thereby indicating position and vector velocity in the 3D space. Each vector map contains information about each particle, including position and velocity, as computed by the displacement in 3D volume, such as using x,y,z coordinates. The position and velocity map Vp for the considered particles is shown in a rectilinear x,y,z coordinate system, but may alternatively be organized in any 3D space representation system, including spherical coordinates, or cylindrical coordinates, where a translated axis of rotation may be identified as part of the coordinate system, either before or after classification, as will be described.

In one embodiment of the invention, a series of images are sequentially acquired with an acquisition rate sufficiently high such that the motion and velocity of each particle can be discerned in the acquired images, such as was described for FIG. 5E. In this example of the invention, the acquired images are analyzed in pairs, and each particle is classified by velocity and vector direction of movement over time. This analysis would result in the particle velocity map shown in FIG. 5A (for the simplified example of 2D only for illustrative clarity), the movement of each of the particles is shown as a plurality of vectors, each vector indicating particle direction and velocity in 3D space. For clarity of description, the present discussion will be directed to a 2D slice such as FIG. 5A in the y-z plane, however it is understood that the turbulent flow estimation algorithm will be directed to the 3D case, with the algorithm directed to operation in the x-y-z 3D volume.

In another embodiment of the invention, the particles in x,y,z space each have a velocity and vector which are generated such as by a computer, and form a virtual data set which may be modeled in the same manner as a directly acquired data set by using the subsequent steps of the algorithm.

In a subsequent step 403 of FIG. 4, a uniform density function is applied to the particle velocity map of FIG. 5A, where a user-selectable control adjusts the analysis density in a 3D volume, such that particle densities above a threshold density are removed from the analysis volume, and particles below a threshold density are unchanged. The density reduction may be done using an algorithm which removes particles closer to each other than a separation distance derived from the threshold density, or any algorithm which generates a generally uniform density field of particles in 3D space. In the example particle distribution of FIG. 5A, the identified regions 501A and 503A have a higher than threshold density of particles compared to the surrounding volume. In this example, a density reduction step is performed, resulting in the considered particles remaining as shown in FIG. 5B, where corresponding regions 501B and 503C now have reduced density equal to the threshold density.

Figure 5B:
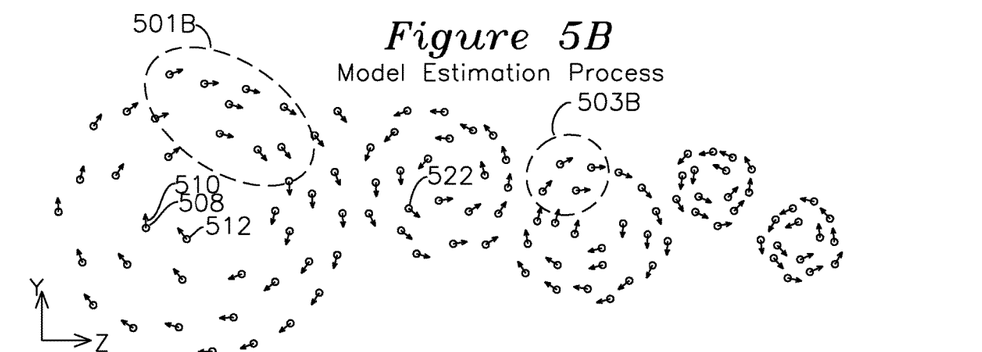
FIG. 5B shows the example distribution of particles after normalization to uniform density.

FIG. 5B shows a post-density normalization step example where particles 508, 512, and 522 in a field of particles have motions shown as indicated by the vector arrows. The vector magnitudes may be estimated by analysis of pairs of acquired images to generate the vectors shown in FIG. 5A associated with each particle, as was previously described.

Figure 5C:
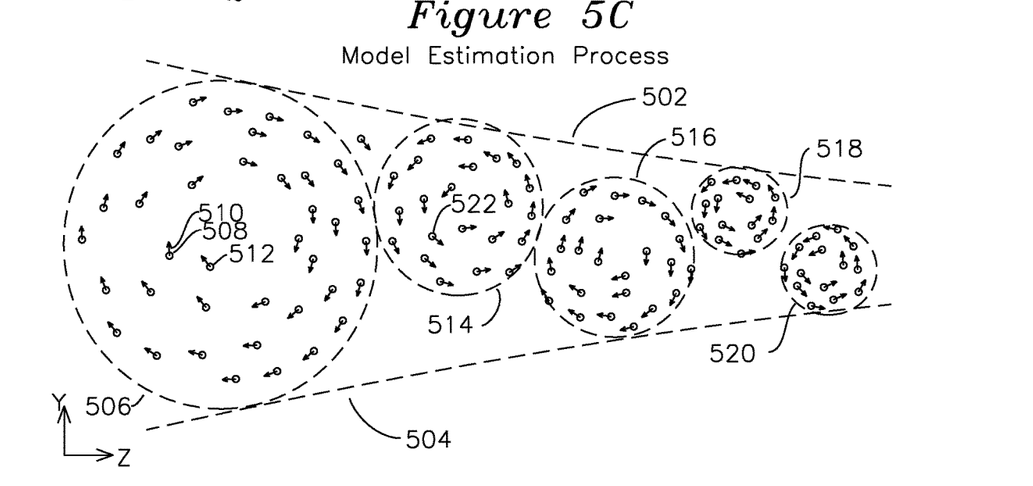
FIG. 5C shows identification of extents of particles of FIG. 5B.
Figure 5D:
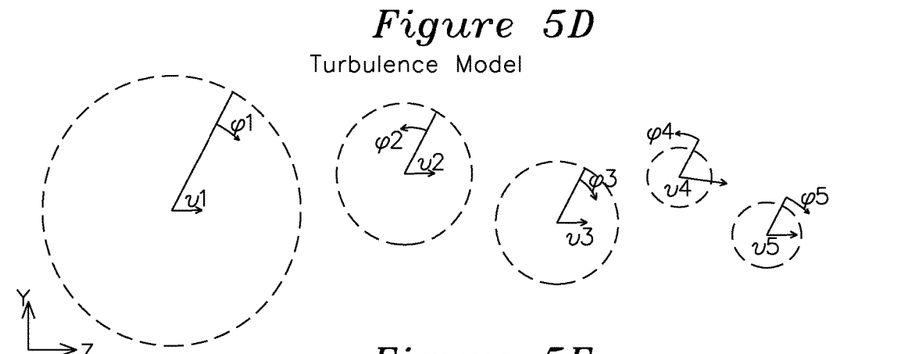
FIG. 5D shows a turbulent flow model for the particles of FIG. 5B using continuous surface primitive shapes.
Figure 5E:
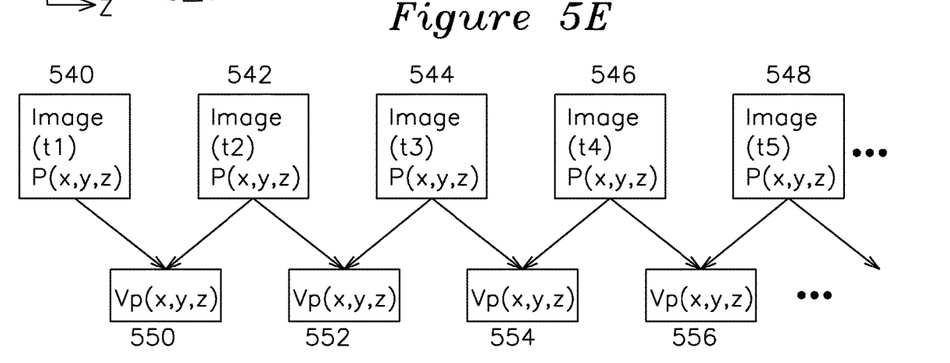
FIG. 5E shows the generation of particle position and velocity profiles using pairs from a sequence of acquired 3D images.

FIG. 5C shows an example first classification step using the example case of particles and velocity vectors of FIG. 5B. A possible first classification step may be to determine the extents of turbulent flow, shown as boundaries 502 and 504. Turbulent flow is known to have a logarithmic convergence to the center of the flow (the z axis in this example) following a flow disruption, with the length of the logarithmic tail along z related to the flow velocity Reynolds number, magnitude of the discontinuity of flow disruption, and other parameters of fluid dynamics. A second classification step may be to identify regions of same-behavior flow, such as the circular boundary regions 506, 514, 516, 518, and 520 delineated by circular flow in each respective boundary. In this classification step, the primary shapes which will be used for modeling the turbulent flow are identified by selection of a collection of particular particles contained by an outermost boundary, based on particles which would fit the model of forming a primitive shape from the outermost collection of such particles, in a 3D volume, although 2D is shown for clarity in FIG. 5C.

Primitive shapes which are formed from the particles of FIG. 5B may be generated as discrete primitive shapes or as continuous primitive shapes. For discrete primitive shapes, particles which form the outermost extents of eddy flows which rotate in the same direction and as part of the same system of particles are used as vertices of a polyhedron, with the inner particles either discarded from the model (if they are rotating substantially radially with a radial velocity which is consistent with the radial velocity model v=rφ where r is the radial distance from the center of rotation and φ is the rotational rate in radians per second about an axis of rotation specified as a line in the x,y,z coordinate system. The collection of such particles used to form the vertices of each discrete primitive shape may also be referred to as "primary elements". In an alternative embodiment, inner particles are selected which form a series of concentric shells, each shell formed by a plurality of particles which is contained within an outer extent of particles forming a separate shell, each shell having its own particular rotational rate with respect to a respective shell center point and axis of rotation. In this manner, particles which have the same rotational rate about a center may result in a simplified model comprising a single primitive shape, whereas particles which have a different rotational rate within an enclosed eddy flow extent may be represented by a plurality of enclosed shells, each of which reflect the separate rotational rate and axis of each enclosed shell.

Figure 6A:
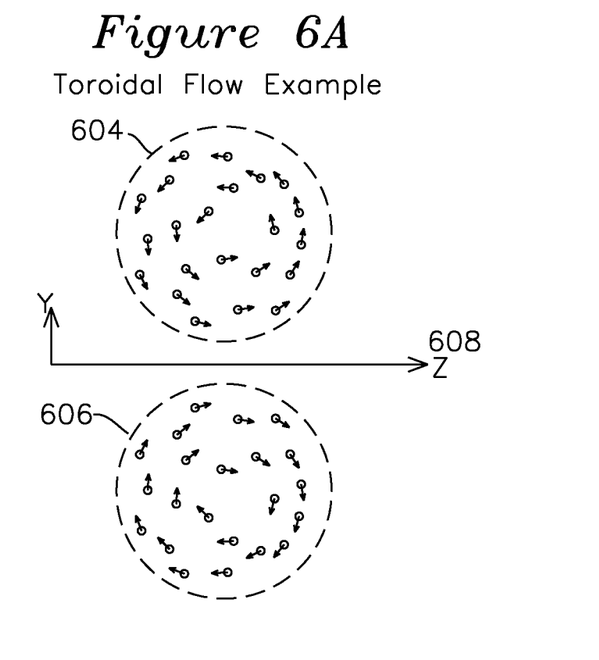
FIG. 6A shows an example set of particles having a toroidal flow profile.

A system of continuous surface primitive objects is shown in the example of FIG. 5C, where the collection of particles enclosed by region 506 may be modeled as a circular solid in 2D (in a typical 3D volume for a rectangular flow, this primitive shape may be an sphere or an ellipsoid with a diameter in the y-z plane which varies in diameter along the x axis). For the case of a circular outer flow near a boundary with an uninterrupted central flow, such the flow of FIG. 6A in 2D through a circular pipe (not shown), the circular flow may be circularly symmetric about any plane which includes the Z axis 608 corresponding to a central axis of the circular pipe (not shown), in which case the turbulent flow may be modeled as a toroid with flow boundaries 604 as shown in FIG. 6A. As with the discrete primitive shapes, the continuous primitive shapes may also be formed into a series of semi-concentric continuous primitive shapes, each with a different rotational rate φ radians per second.

Figure 5F:
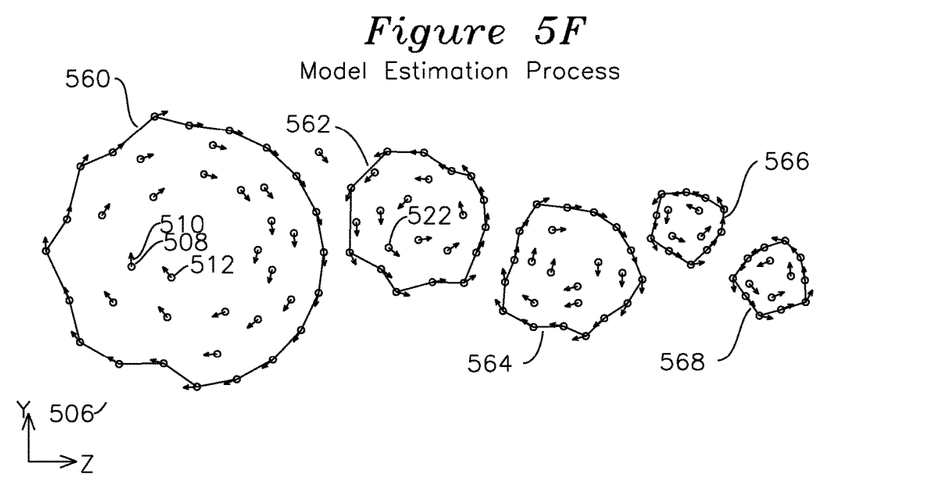
FIG. 5F shows a turbulent flow model for the particles of FIG. 5B using discrete surface primitive shapes.

FIG. 5F shows a flow which has been formed into discrete polyhedron primitive shapes (shown in 2D for clarity only), where the outer boundary of particles with the same directional flow are formed into discrete polyhedron shapes 560, 562, 564, 566, and 568, each primitive polyhedron shape having its own rotational rate φ and translational characteristic and a collection of surface-defining vertices formed from the primary elements as described previously.

Returning to the identified flow boundaries 506, 514, 516, 518, and 520 of FIG. 5C, each of these regions may be modeled in 3D as an ellipsoid or sphere, each of which has a center point C(x,y,z), a velocity v, and a rotational velocity φ. In addition, each of these parameters may also have a time-dependent term which describes the evolution over time, such that the diameter of the primitive shape may shrink or grow, the rotational velocity about center C(x,y,z) may change with time, as well as any other time-dependent description of the turbulent flow.

Figure 6B:
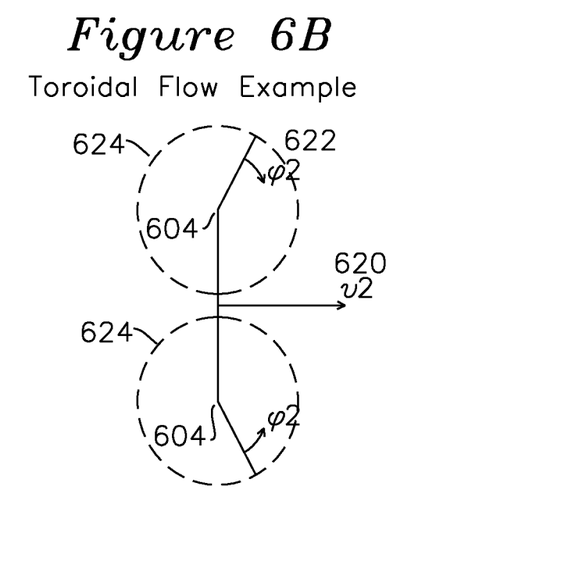
FIG. 6B shows a turbulent flow model for the particles of FIG. 6A.

FIG. 6A shows example toroidal flow boundaries 604 and 606, where the modeled flow is shown in FIG. 6B as a torus 624 with a rotation about a center circle 604, where the primitive shape is a solid which rotates with a rotational rate φ2 622 and propagates with velocity v2 620 with respect to (x,y,z).

Figure 7A:
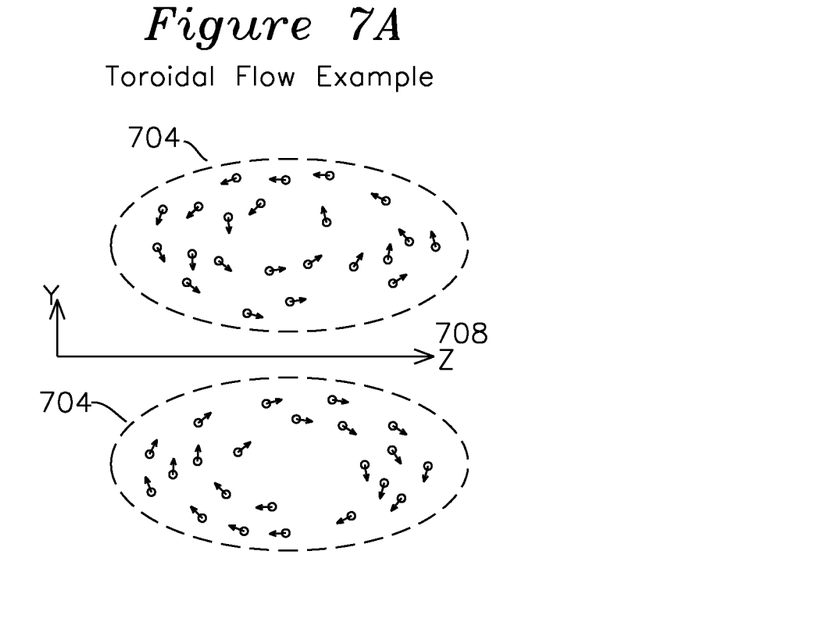
FIG. 7A shows particles having an elliptical velocity profile.
Figure 7B:
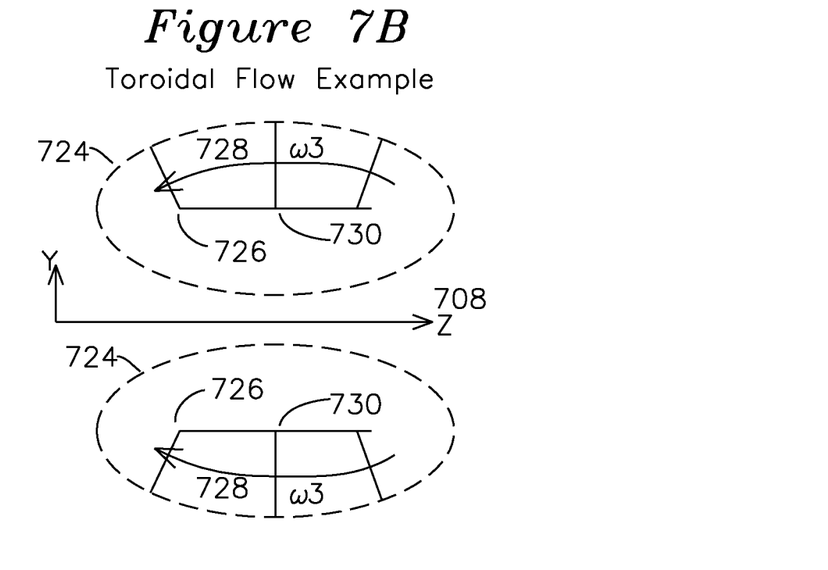
FIG. 7B shows a turbulent flow model for the particles of FIG. 7A.

FIG. 7A shows an example of an eddy flow boundary 704 for a toroidal flow, where the eddy flow extent boundary 704 is determined based on the enclosed particles circulating as shown with respect to the axis 708 of the pipe (not shown) enclosing the flow. FIG. 7B shows the resulting turbulent flow model for the continuous flattened torus primitive shape, which may be understood in cross section (plane Y-Z as shown) as a pair of ellipsoids 724 (which are both part of the torus in the X-Y plane) where the model describes movement which is swept in the trajectory of 728 through the entire circumference of the torus 724, as shown. The parametric description of the flattened toroid 724 may include the center point 730, one or more foci 726, a scale factor over time, and a velocity and direction for the primitive shape with reference to the center 730.

Although the examples for primitive shapes including continuous primitive shapes such as a 3D sphere, ellipsoid, and torus, the primitive shapes may alternatively be formed from polyhedrons described by the outer extent particles of boundaries 506 of FIG. 5C, or 604 of FIG. 6A, each primitive shape having an associated rotational velocity (which may be time-dependent), linear velocity (which may also be time dependent), time-dependent scaling factor, each of which is operative in the (x,y,z) 3D space as previously described.

The rotating solid model comprising the plurality of primitive shapes thereby provides a model for turbulent flow which incorporates the behavior of the measured flow.

Many variants are possible. For example, for ease of computation, it may also be possible to use flow symmetry to describe half of the model and utilize the flow symmetry to describe the other half.

In another example of the invention, the particles are infused into the fluid in a static state without flow, and the flow initializes from no flow to a flow condition with the imaging and identification of primitive shapes occurring concurrent with the initiation of flow. In this example embodiment, the formation and evolution of eddy flow patterns and turbulent flow patterns may be identified and modeled through their evolution from a no-flow initial condition into a steady state set of turbulence patterns.

In another example of the invention, the method for flow modeling relies on particle descriptions in a data array rather than image capture of the particles. In this variation, the data array may be constructed using actual measurements from observation of flow phenomena, synthetic data derived from a flow measurement or flow model, or machine-generated data in the form of a set of particle position and associated vector velocity. Additionally, the data array may be generated by using a combination of measurement data, synthetic data derived from the measurement data, or supplemental data which is added to the data array. In this example, the process for generating a model to estimate the particle behavior may comprise:

a particle generation step of generating a data array which provides a particle position and velocity of each particle;

an optional particle density reduction step whereby the particle positions of said generation step are reduced to a threshold density in regions where said particle density exceeds said threshold density;

a particle model step whereby said particles are grouped as belonging to an eddy flow group, the positions of said particles in each said eddy flow group used to form a plurality of primitive shapes, each said primitive shape having vertices defined by a subset of said particle positions.

In another variation of the invention, one or more "secondary elements" may be identified in the form of a particular one of the primary elements of a vertex or a surface of the primitive shape which travels along the eddy flow, rotating until it is at a point closest to a subsequent eddy flow, then transferring to the subsequent eddy flow by associating the secondary element to a surface of a primary shape of the subsequent eddy flow or to a primary element of the subsequent eddy flow, the secondary element thereafter rotating with the primitive shape of the subsequent eddy flow until transferring to another subsequent eddy flow. In this manner, the secondary element may perform as a tracing or tracking element, indicating the rotational characteristics of each eddy flow. Alternatively, a plurality of secondary elements may be provided as visual aids in the flow model.

The proceeding has been a description of the preferred embodiment of the invention. It will be appreciated that deviations and modifications can be made without departing from the scope of the invention, which is defined by appended claims.

I claim:

1. A flow imaging system having a plurality of cameras directed at a liquid flow having suspended entrained particles enclosed within a pipe, each camera having an orthogonal view with respect to a central axis of the pipe, the particles distinguishable from the liquid in the pipe, the cameras capturing a sequence of images of the entrained particles, the imaging system forming a model of the liquid flow whereby:
    each of the cameras captures a plurality of images of the entrained particles;
    the imaging system examines each said particle in successive images of the sequence of images and further associates each particle with a position and velocity vector estimating the position and velocity of each said particle;
    the imaging system forming a subset of particle positions from the plurality of particle positions by eliminating particles in regions where a particle density exceeds a threshold density;
    grouping said subset of particles into one or more eddy flow groups, where positions of said particles in each said eddy flow group form a plurality of primitive shapes, each said primitive shape having vertices defined by a subset of said particle positions;
    said imaging system thereby providing a plurality of primitive shapes from said imaged particles.

2. The flow imaging system of claim 1 wherein said threshold density is derived from a peak particle density over a first volume compared to an average particle density over a larger volume.

3. The flow imaging system of claim 1 wherein particles are selected which have a greatest separation distance from a center of said eddy flow group.

4. The flow imaging system of claim 1 wherein said threshold density is a user settable threshold.

5. The flow imaging system of claim 1 wherein said particles are present in the fluid prior to the initiation of said turbulent flow.

6. The flow imaging system of claim 1 wherein said primitive shapes are polyhedron primitive shapes, each said polyhedron primitive shape having vertices formed by said particle locations, at least one of said polyhedron primitive shapes surrounding and enclosing another polyhedron primitive shape.

7. The flow imaging system of claim 1 where each said primitive shape has a rotational velocity and a translational velocity.

8. The flow imaging system of claim 1 where said primitive shape positions is further modified by the removal of any particles which are enclosed by said primitive shape.

9. The flow imaging system of claim 1 wherein said entrained particles are at least one of: smoke, reflective particles, balls, dye, or metal flakes, the entrained particles having substantially the same density as the flow to be characterized.

10. The flow imaging system of claim 1 wherein at least one secondary element is formed from a vertex of a primitive shape, the secondary element following the trajectory of a vertex of the initial primitive shape until reaching a point closest to the vertex of a subsequent primitive shape, the secondary element thereafter following the trajectory of a closest vertex of each subsequent primitive shape through the sequence of captured images.

11. A flow imaging system for forming a turbulent flow list of primitives, the flow imaging system operative on a pipe having flow constrictions, the flow comprising a liquid with entrained particles, the flow imaging system comprising:
    a plurality of image acquisition cameras arranged about the pipe in orthogonal positions with respect to a central axis of the pipe and acquiring a successive set of images of the particles entrained in the flow, whereby said particles have an associated particle velocity and angle derived from pairs of said successive set of images;
    the flow imaging system reducing the number of particles in each image through a particle density reduction where regions having a density of particle positions which are greater than a particle threshold density are not considered, and particle positions which are lower than a threshold density are considered;
    said list of primitives formed from groups of said considered particles grouped into an eddy flow group, the positions of each eddy flow group used to form a primitive shape, each primitive shape having at least a linear velocity and a rotational velocity.

12. The flow imaging system of claim 11 wherein said eddy flow group is determine by examination of adjacent pairs of images separated by the duration of an acquisition interval of said images.

13. The flow imaging system of claim 11 wherein said particle threshold density is determined based on a peak density over a first volume and an average density over a larger volume.

14. The flow imaging system of claim 11 wherein each primitive shape if formed from the selection of particles which have a greatest separation distance from a center of said eddy flow group.

15. The flow imaging system of claim 11 wherein said threshold density comprises a user settable threshold.

16. The flow imaging system of claim 11 wherein said entrained particles have a density equal to the density of a surrounding liquid to be characterized.

17. The flow imaging system of claim 1 wherein said primitive shapes include at least one of: a sphere, an ellipsoid, or a torus.

18. The flow imaging system of claim 11 where each said primitive shape has a rotational velocity and a translational velocity.

19. The flow imaging system of claim 1 where each said primitive shape includes only vertices.

20. The flow imaging system of claim 11 wherein said entrained particles are at least one of: smoke, reflective particles, balls, dye, or metal flakes, the entrained particles having substantially the same density as the flow to be characterized.

21. The flow imaging system of claim 11 wherein at least one secondary element is formed from a vertex of a primitive shape, the secondary element following the trajectory of a vertex of the initial primitive shape until reaching a point closest to the vertex of a subsequent primitive shape, the secondary element thereafter following the trajectory of a closest vertex of each subsequent primitive shape.

22. A flow imaging system for modeling a liquid flowing in a pipe with flow restrictions, the liquid having entrained particles which are visible to an imaging camera;

a plurality of imaging cameras examining the liquid flow and entrained particles from outside of the pipe, the imaging cameras positioned to provide orthogonal cross section views of the entrained particles in the flow, the flow imaging system:

capturing a plurality of images of the entrained particles with the imaging cameras, the image cameras examining successive images to determine, for each particle, an associated particle velocity or particle velocity vector;

performing a particle density reduction whereby the particle positions are reduced to a threshold density in regions where said particle density exceeds said threshold density;

forming a particle model whereby said particles which exceed said threshold density are grouped as belonging to an eddy flow group, the positions of said particles in each said eddy flow group used to form a plurality of primitive shapes, each said primitive shape having vertices defined by a subset of said particle positions.

* * * * *